United States Patent
Gandhi et al.

(10) Patent No.: US 9,808,001 B1
(45) Date of Patent: Nov. 7, 2017

(54) MICROBICIDAL COMPOSITION

(71) Applicants: Dow Global Technologies LLC, Midland, MI (US); Rohm and Haas Company, Collegeville, PA (US)

(72) Inventors: Usha Gandhi, Hatboro, PA (US); Christine McInnis, Blue Bell, PA (US); Kiran Pareek, Bensalem, PA (US); Paul O. Schook, Lake Zurich, IL (US); Nigel G. Watson, Chadds Ford, PA (US); Terry Michael Williams, Lower Gwynedd, PA (US); Bei Yin, Phoenixville, PA (US)

(73) Assignees: ROHM AND HAAS COMPANY, Philadelphia, PA (US); DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 15/662,457

(22) Filed: Jul. 28, 2017

Related U.S. Application Data

(62) Division of application No. 15/026,136, filed as application No. PCT/US2014/058954 on Oct. 3, 2014.

(60) Provisional application No. 61/886,344, filed on Oct. 3, 2013.

(51) Int. Cl.
*A61K 31/54* (2006.01)
*A01N 25/30* (2006.01)
*A01N 43/88* (2006.01)
*A01N 43/84* (2006.01)
*A01N 35/08* (2006.01)

(52) U.S. Cl.
CPC ............ *A01N 25/30* (2013.01); *A01N 35/08* (2013.01); *A01N 43/84* (2013.01); *A01N 43/88* (2013.01)

(58) Field of Classification Search
None
See application file for complete search history.

(56) References Cited

U.S. PATENT DOCUMENTS

2013/0203825 A1* 8/2013 Premachandran ..... A01N 25/04
514/373

\* cited by examiner

*Primary Examiner* — Dennis Heyer
*Assistant Examiner* — Daniel M Podgorski
(74) *Attorney, Agent, or Firm* — Kenneth Crimaldi

(57) ABSTRACT

A synergistic microbicidal composition having two components. The first component is a nonionic surfactant with structure: $R^2O(CH_2CH(CH_3)O)_3(CH_2CH_2O)_5H$, where $R^2$ is a mixture of $C_8$-$C_{14}$ linear alkyl groups. The second component is 2-bromo-2-nitropropane-1,3-diol. The weight ratio of the nonionic surfactant to 2-bromo-2-nitropropane-1,3-diol is from 1:0.08 to 1:0.12 or 1:0.2 to 1:1.8286.

2 Claims, No Drawings

MICROBICIDAL COMPOSITION

This invention relates to microbicidal compositions containing 2-bromo-2-nitropropane-1,3-diol (BNPD), tetrahydro-3,5-dimethyl-2H-1,3,5-thiadiazine-2-thione (DAZOMET) or BIOBAN P-1487 (ca. 81:5 mixture of 4-(2-nitrobutyl)morpholine and 4,4'-(2-ethyl-2-nitrotrimethylene)dimorpholine, respectively) and a surfactant.

A composition containing 5-chloro-2-methylisothiazolin-3-one, 2-methylisothiazolin-3-one and a nonionic dispersant is disclosed in U.S. Pat. No. 4,295,932. The composition contains a 3:1 mixture of 5-chloro-2-methylisothiazolin-3-one and 2-methylisothiazolin-3-one, and a copolymer of ethylene oxide and propylene oxide which appears to have the same composition as PLURONIC L61 or TERGITOL L61 dispersant. However, there is a need for combinations of microbicides having synergistic activity against various strains of microorganisms to provide effective control of the microorganisms. Moreover, there is a need for such combinations containing lower levels of individual microbicides for environmental and economic benefit. The problem addressed by this invention is to provide such synergistic combinations of microbicides.

STATEMENT OF THE INVENTION

The present invention is directed to a synergistic microbicidal composition comprising: (a) a nonionic surfactant with structure:

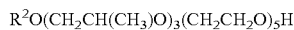

where $R^2$ is a mixture of $C_8$-$C_{14}$ linear alkyl groups; and (b) 2-bromo-2-nitropropane-1,3-diol; wherein a weight ratio of said nonionic surfactant to 2-bromo-2-nitropropane-1,3-diol is from 1:0.08 to 1:0.12 or 1:0.2 to 1:1.8286.

The present invention is further directed to a synergistic microbicidal composition comprising: (a) a nonionic surfactant with structure:

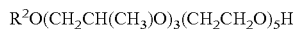

where $R^2$ is a mixture of $C_8$-$C_{14}$ linear alkyl groups; and (b) tetrahydro-3,5-dimethyl-2H-1,3,5-thiadiazine-2-thione; wherein a weight ratio of said nonionic surfactant to tetrahydro-3,5-dimethyl-2H-1,3,5-thiadiazine-2-thione is from 1:0.0024 to 1:0.4571.

The present invention is further directed to a synergistic microbicidal composition comprising: (a) a nonionic surfactant with structure:

where $R^1$ is a $C_8$ alkyl group; and (b) a mixture of 4-(2-nitrobutyl)morpholine and 4,4'-(2-ethyl-2-nitrotrimethylene)dimorpholine in a weight ratio of 81:5; wherein a weight ratio of said nonionic surfactant to said mixture is from 1:0.0006 to 1:0.2743.

The present invention is further directed to methods for inhibiting the growth of microorganisms in aqueous media by adding to an aqueous medium a nonionic surfactant as described herein and 2-bromo-2-nitropropane-1,3-diol, tetrahydro-3,5-dimethyl-2H-1,3,5-thiadiazine-2-thione or a ca. 81:5 mixture of 4-(2-nitrobutyl)morpholine and 4,4'-(2-ethyl-2-nitrotrimethylene)dimorpholine in the ratios described herein.

DETAILED DESCRIPTION OF THE INVENTION

"BNPD" is 2-bromo-2-nitropropane-1,3-diol, "DAZOMET" has as an active ingredient tetrahydro-3,5-dimethyl-2H-1,3,5-thiadiazine-2-thione (CAS No. 533-74-4) and "BIOBAN P-1487" is an approximately 81:5 (weight) mixture of 4-(2-nitrobutyl)morpholine and 4,4'-(2-ethyl-2-nitrotrimethylene)dimorpholine. As used herein, the following terms have the designated definitions, unless the context clearly indicates otherwise. The term "microbicide" refers to a compound capable of inhibiting the growth of or controlling the growth of microorganisms; microbicides include bactericides, fungicides and algaecides. The term "microorganism" includes, for example, fungi (such as yeast and mold), bacteria and algae. The following abbreviations are used throughout the specification: ppm=parts per million by weight (weight/weight), mL=milliliter. Unless otherwise specified, temperatures are in degrees centigrade (° C.), references to percentages are percentages by weight (wt %) and amounts and ratios are on an active ingredient basis, i.e., total weight of BNPD, DAZOMET or BIOBAN P-1487 active ingredients and the nonionic surfactant. Numbers of polymerized units of propylene oxide or ethylene oxide are number averages.

Preferably, the weight ratio of the nonionic surfactant with structure:

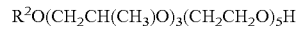

where $R^2$ is a mixture of $C_8$-$C_{14}$ linear alkyl groups to BNPD is from 1:0.2286 to 1:1.18286.

The present invention is further directed to a method for inhibiting the growth of mold, preferably *C. albicans*, in an aqueous medium by adding: (a) a nonionic surfactant with structure:

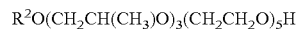

where $R^2$ is a mixture of $C_8$-$C_{14}$ linear alkyl groups; and (b) BNPD; wherein a weight ratio of said nonionic surfactant to BNPD is from 1:0.08 to 1:0.12 or 1:0.2 to 1:1.8286, preferably from 1:0.2286 to 1:1.18286.

Preferably, the weight ratio of the nonionic surfactant with structure:

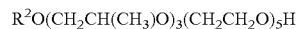

where $R^2$ is a mixture of $C_8$-$C_{14}$ linear alkyl groups to DAZOMET is from 1:0.0114 to 1:0.4571.

The present invention is further directed to a method for inhibiting the growth of *S. aureus*, in an aqueous medium by adding: (a) a nonionic surfactant with structure:

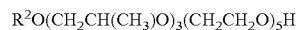

where $R^2$ is a mixture of $C_8$-$C_{14}$ linear alkyl groups; and (b) DAZOMET; wherein a weight ratio of said nonionic surfactant to DAZOMET is from 1:0.0114 to 1:0.4571.

Preferably, the weight ratio of the nonionic surfactant with structure:

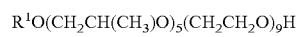

where $R^1$ is a $C_8$ alkyl group to BIOBAN P-1487 is from 1:0.0160 to 1:0.2743.

The present invention is further directed to a method for inhibiting the growth of fungi, preferably *A. niger*, in an aqueous medium by adding: (a) a nonionic surfactant with structure:

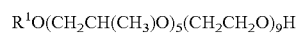

where $R^1$ is a $C_8$ alkyl group to BIOBAN P-1487 is from 1:0.0160 to 1:0.2743.

$R^2$ is a mixture of $C_8$-$C_{14}$ linear alkyl groups. Preferably, the $C_8$-$C_{14}$ linear alkyl groups comprise from 50 to 85 wt % $C_8$-$C_{10}$ linear alkyl groups and 15 to 50 wt % $C_{12}$-$C_{14}$ linear alkyl groups, preferably from 60 to 75 wt % $C_8$-$C_{10}$ linear alkyl groups and 25 to 40 wt % $C_{12}$-$C_{14}$ linear alkyl groups, preferably about 70 wt % $C_8$-$C_{10}$ linear alkyl groups and about 30 wt % $C_{12}$-$C_{14}$ linear alkyl groups. Preferably, the linear alkyl groups are derived from seed oil. Preferably, $R^1$ is 2-ethylhexyl.

Preferably, each of the compositions is substantially free of microbicides other than the nonionic surfactant and BNPD, DAZOMET or BIOBAN P-1487, i.e., it has less than 1 wt % of microbicides other than the nonionic surfactant and BNPD, DAZOMET or BIOBAN P-1487 based on total weight of active ingredients, preferably less than 0.5 wt %, preferably less than 0.2 wt %, preferably less than 0.1 wt %. Preferably, when the nonionic surfactant and BNPD, DAZOMET or BIOBAN P-1487 are added to an aqueous medium, the medium is substantially free of other microbicides, i.e., it has less than 1 wt % of microbicides other than the nonionic surfactant and BNPD, DAZOMET or BIOBAN P-1487 based on total weight of active ingredients, preferably less than 0.5 wt %, preferably less than 0.2 wt %, preferably less than 0.1 wt %.

The compositions of this invention may contain other ingredients, e.g., defoamers and emulsifiers. The microbicidal compositions of the present invention can be used to inhibit the growth of microorganisms or higher forms of aquatic life (such as protozoans, invertebrates, bryozoans, dinoflagellates, crustaceans, mollusks, etc) by introducing a microbicidally effective amount of the compositions into an aqueous medium subject to microbial attack. Suitable aqueous media are found in, for example: industrial process water; electrocoat deposition systems; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; personal care products such as wipes, lotions, sunscreen, conditioners, creams, and other leave-on applications; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

The specific amount of the microbicidal compositions of this invention necessary to inhibit or control the growth of microorganisms in an application will vary. Amounts of the compositions of the present invention are given on the basis of active ingredients (i.e., nonionic surfactant and BNPD, DAZOMET or BIOBAN P-1487). For BNPD/surfactant used in paper applications, preferably the concentration is 2 to 50 ppm, preferably 5 to 40 ppm. For BNPD/surfactant used in oil and gas drilling applications, preferably the concentration is 10 to 500 ppm, preferably 20 to 350 ppm. For BNPD/surfactant used in metalworking fluids, preferably the concentration is 150 to 2000 ppm, preferably 300 to 1500 ppm. For BIOBAN P-1487/surfactant used in metalworking fluids, preferably the concentration is 600 to 1800 ppm, preferably 800 to 1500 ppm. For BIOBAN P-1487/surfactant used in fuel applications, preferably the concentration is 300 to 4000 ppm, preferably 500 to 3000 ppm. Fuel applications include the preservation of hydrocarbons for fuel, e.g., bioethanol applications, diesel storage tank preservation and general fuel tank preservation. In a method of this invention, a composition is treated to inhibit microbial growth by adding, together or separately, the nonionic surfactant and BNPD, DAZOMET or BIOBAN P-1487, in amounts that would produce the concentrations indicated above.

EXAMPLES

Surfactants and biocides were evaluated for synergy by determining the synergy index (S.I.) of the combination. Synergy index was calculated based on minimum inhibitory concentrations (MIC) of two antimicrobial compounds (A and B) alone and in combinations. The tests organisms were Gram negative bacteria (*Pseudomonas aeruginosa* ATCC #15442), Gram positive bacteria (*Staphylococcus aureus* ATCC #6538), yeast (*Candida albicans* ATCC#10203) and mold (*Aspergillus niger* ATCC#16404). Contact time for the bacteria was 24 and 48 hours, yeast was 48 and 72 hrs, and 3 and 7 days for mold. The test was carried out in 96 well microtiter plates.

Surf. A $R^1O(CH_2CH(CH_3)O)_5(CH_2CH_2O)_9H$, where $R^1$ is 2-ethylhexyl

Surf. D $R^2O(CH_2CH(CH_3)O)_3(CH_2CH_2O)_5H$

Surf. E $R^2O(CH_2CH(CH_3)O)_3(CH_2CH_2O)_7H$

In Surf. D and Surf. E, $R^2$ is a mixture of $C_8$-$C_{14}$ linear alkyl groups (70% $C_8$-$C_{10}$ linear alkyl and 30% $C_{12}$-$C_{14}$ linear alkyl)

| | Inoculums Used Inoculum Size of organisms (CFU/ml) | | | |
|---|---|---|---|---|
| Surfactants | Staphylococcus aureus ATCC# 6538 | Pseudomonas aeruginosa ATCC# 15442 | Aspergillus niger ATCC# 16404 | Candida albicans ATCC# 10203 |
| Surf. A | 1.156E+06 | 8.134E+07 | 1.156E+06 | 1.156E+06 |
| Surf. D | 1.808E+05 | 1.156E+08 | 1.156E+06 | 5.726E+05 |
| Surf. E | 1.808E+06 | 5.727E+07 | 5.726E+05 | 1.808E+06 |

TABLE 4

| Media Used Media Used for testing | | | |
|---|---|---|---|
| Staphylococcus aureus ATCC# 6538 | Pseudomonas aeruginosa ATCC# 15442 | Aspergillus niger ATCC# 16404 | Candida albicans ATCC# 10203 |
| 10% Tryptic soy broth | 10% Tryptic soy broth | Potato dextrose broth | Potato dextrose broth |

The pH of the Triptic soy broth was 7.3 and the Potato dextrose broth was 5.1.

The test results for demonstration of synergy of the MIC combinations are shown in the tables below. Each table shows the results for combinations of two components against the microorganisms tested with incubation times; the end-point activity in ppm measured by the MIC for compound A alone (CA), for component B alone (CB), and the mixture (Ca) and (Cb); the calculated SI value; and the range of synergistic ratios for each combination tested. SI is calculated as follows:

$$Ca/CA + Cb/CB = \text{Synergy Index ("SI")}$$

Wherein:

CA=concentration of compound A in ppm, acting alone, which produced an end point (MIC of Compound A).

Ca=concentration of compound A in ppm, in the mixture, which produced an end point.

CB=concentration of compound B in ppm, acting alone, which produced an end point (MIC of Compound B).

Cb=concentration of compound B in ppm, in the mixture, which produced an end point.

When the sum of Ca/CA and Cb/CB is greater than one, antagonism is indicated. When the sum is equal to one, additivity is indicated, and when less than one, synergism is demonstrated.

The ratio ranges at which BNPD, DAZOMET or BIOBAN P-1487 and the surfactants were tested are as summarized in the following tables:

BNPD with Surf. A

| Organism | ATCC# | From | To | Ratio Range |
|---|---|---|---|---|
| Staphylococcus aureus | 6538 | 0.02:20,000 | 100:218.75 | 1:0.000001-1:0.45714 |
| Aspergillus niger | 16404 | 0.2:20,000 | 1,000:218.75 | 1:0.00001-1:4.5714 |
| Candida albicans | 10203 | 0.2:20,000 | 1,000:218.75 | 1:0.00001-1:4.5714 |
| Pseudomonas aeruginosa | 15442 | 0.02:20,000 | 100:218.75 | 1:0.000001-1:0.45714 |

BNPD with Surf. E

| Organism | ATCC# | From | To | Ratio Range |
|---|---|---|---|---|
| Staphylococcus aureus | 6538 | 0.02:20,000 | 100:218.75 | 1:0.000001 1:0.45714 |
| Aspergillus niger | 16404 | 0.2:20,000 | 1,000:218.75 | 1:0.00001-1:4.5714 |
| Candida albicans | 10203 | 0.2:20,000 | 1,000:218.75 | 1:0.00001-1:4.5714 |
| Pseudomonas aeruginosa | 15442 | 0.02:20,000 | 100:218.75 | 1:0.000001-1:0.45714 |

BNPD with Surf. D

| Organism | ATCC# | From | To | Ratio Range |
|---|---|---|---|---|
| Staphylococcus aureus | 6538 | 0.02:20,000 | 100:218.75 | 1:0.000001-1:0.45714 |
| Aspergillus niger | 16404 | 0.2:20,000 | 1,000:218.75 | 1:0.00001-1:4.5714 |
| Candida albicans | 10203 | 0.2:20,000 | 1,000:218.75 | 1:0.00001-1:4.5714 |
| Pseudomonas aeruginosa | 15442 | 0.02:20,000 | 100:218.75 | 1:0.000001-1:0.45714 |

BIOBAN P-1487 with Surf. A

| Organism | ATCC # | From | To | Ratio Range |
|---|---|---|---|---|
| Staphylococcus aureus | 6538 | 0.002:20,000 | 10:218.75 | 1:0.0000001-1:0.0457143 |
| Aspergillus niger | 16404 | 0.02:20,000 | 100:218.75 | 1:0.000001-1:0.45714 |
| Candida albicans | 10203 | 0.02:20,000 | 100:218.75 | 1:0.000001-1:0.45714 |
| Pseudomonas aeruginosa | 15442 | 0.02:20,000 | 100:218.75 | 1:0.000001-1:0.45714 |

BIOBAN P-1487 with Surf. E

| Organism | ATCC # | From | To | Ratio Range |
|---|---|---|---|---|
| Staphylococcus aureus | 6538 | 0.02:20,000 | 100:218.75 | 1:0.000001-1:0.45714 |
| Aspergillus niger | 16404 | 0.02:20,000 | 100:218.75 | 1:0.000001-1:0.45714 |
| Candida albicans | 10203 | 0.02:20,000 | 100:218.75 | 1:0.000001-1:0.45714 |
| Pseudomonas aeruginosa | 15442 | 0.02:20,000 | 100:218.75 | 1:0.000001-1:0.45714 |

BIOBAN P-1487 with Surf. D

| Organism | ATCC # | From | To | Ratio Range |
|---|---|---|---|---|
| Staphylococcus aureus | 6538 | 0.02:20,000 | 100:218.75 | 1:0.000001-1:0.45714 |
| Aspergillus niger | 16404 | 0.2:20,000 | 1,000:218.75 | 1:0.00001-1:4.5714 |
| Candida albicans | 10203 | 0.02:20,000 | 100:218.75 | 1:0.000001-1:0.45714 |
| Pseudomonas aeruginosa | 15442 | 0.2:20,000 | 1,000:218.75 | 1:0.00001-1:4.5714 |

DAZOMET with Surf. A

| Organism | ATCC # | From | To | Ratio Range |
|---|---|---|---|---|
| Staphylococcus aureus | 6538 | 0.2:20,000 | 1,000:218.75 | 1:0.00001-1:4.5714 |
| Aspergillus niger | 16404 | 0.2:20,000 | 1,000:218.75 | 1:0.00001-1:4.5714 |
| Candida albicans | 10203 | 0.2:20,000 | 1,000:218.75 | 1:0.00001-1:4.5714 |
| Pseudomonas aeruginosa | 15442 | 0.2:20,000 | 1,000:218.75 | 1:0.00001-1:4.5714 |

DAZOMET with Surf. E

| Organism | ATCC # | From | To | Ratio Range |
|---|---|---|---|---|
| Staphylococcus aureus | 6538 | 0.2:20,000 | 1,000:218.75 | 1:0.00001-1:4.5714 |
| Aspergillus niger | 16404 | 0.2:20,000 | 1,000:218.75 | 1:0.00001-1:4.5714 |
| Candida albicans | 10203 | 0.2:20,000 | 1,000:218.75 | 1:0.00001-1:4.5714 |

-continued

DAZOMET with Surf. E

| Organism | ATCC # | From | To | Ratio Range |
|---|---|---|---|---|
| Pseudomonas aeruginosa | 15442 | 0.2:20,000 | 1,000:218.75 | 1:0.00001-1:4.5714 |

DAZOMET with Surf. D

| Organism | ATCC # | From | To | Ratio Range |
|---|---|---|---|---|
| Staphylococcus aureus | 6538 | 0.2:20,000 | 1,000:218.75 | 1:0.00001-1:4.5714 |
| Aspergillus niger | 16404 | 0.2:20,000 | 1,000:218.75 | 1:0.00001-1:4.5714 |
| Candida albicans | 10203 | 0.2:20,000 | 1,000:218.75 | 1:0.00001-1:4.5714 |
| Pseudomonas aeruginosa | 15442 | 0.2:20,000 | 1,000:218.75 | 1:0.00001-1:4.5714 |

A: Surf. A
B: BNPD
Media: 1/10TSB
Inoculum size: 8.134E+07CFU/ml

PPM AI MIC Values (24 hrs)

| Test Organism | Alone CA | Alone CB | Combination Ca | Combination Cb | S.I. | Ratio (Ca:Cb) |
|---|---|---|---|---|---|---|
| Ps. aeruginosa ATCC# 15442 | >20000 | 10 | 20000 | 8 | <1.80 | 1:0.0004 |
| | >20000 | 10 | 10000 | 8 | <1.30 | 1:0.0008 |
| | >20000 | 10 | 5000 | 8 | <1.05 | 1:0.0016 |
| | >20000 | 10 | 2500 | 8 | <0.93 | 1:0.0032 |
| | >20000 | 10 | 1750 | 8 | <0.89 | 1:0.0046 |
| | >20000 | 10 | 875 | 8 | <0.84 | 1:0.0091 |
| | >20000 | 10 | 437.5 | 8 | <0.82 | 1:0.0183 |
| | >20000 | 10 | 218.75 | 8 | <0.81 | 1:0.0366 |

No synergy: A.niger, C.albicans, S.aureus

A: Surf. D
B: BNPD
Media: PDB
Inoculum size: 1.156E+06

PPM AI MIC Values (3rd day)

| Test Organism | Alone CA | Alone CB | Combination Ca | Combination Cb | S.I. | Ratio (Ca:Cb) |
|---|---|---|---|---|---|---|
| A. niger ATCC# 16404 | >20000 | 1000 | 20000 | 500 | <1.50 | 1:0.0250 |
| | >20000 | 1000 | 10000 | 400 | <0.90 | 1:0.0400 |
| | >20000 | 1000 | 10000 | 500 | <1.00 | 1:0.0500 |
| | >20000 | 1000 | 5000 | 500 | <0.75 | 1:0.1000 |
| | >20000 | 1000 | 5000 | 600 | <0.85 | 1:0.1200 |
| | >20000 | 1000 | 5000 | 800 | <1.05 | 1:0.1600 |
| | >20000 | 1000 | 2500 | 500 | <0.63 | 1:0.2000 |
| | >20000 | 1000 | 2500 | 600 | <0.73 | 1:0.2400 |
| | >20000 | 1000 | 2500 | 800 | <0.93 | 1:0.3200 |
| | >20000 | 1000 | 1750 | 600 | <0.69 | 1:0.3429 |
| | >20000 | 1000 | 1750 | 800 | <0.89 | 1:0.4571 |
| | >20000 | 1000 | 875 | 600 | <0.64 | 1:0.6857 |
| | >20000 | 1000 | 875 | 800 | <0.84 | 1:0.9143 |

A: Surf. D
B: BNPD
Media: PDB
Inoculum size: 5.726E+05CFU/ml

PPM AI MIC Values (48 hrs)

| Test Organism | Alone CA | Alone CB | Combination Ca | Combination Cb | S.I. | Ratio (Ca:Cb) |
|---|---|---|---|---|---|---|
| C. albicans ATCC# 10203 | >20000 | 1000 | 20000 | 400 | <1.40 | 1:0.0200 |
| | >20000 | 1000 | 10000 | 400 | <0.90 | 1:0.0400 |
| | >20000 | 1000 | 10000 | 500 | <1.00 | 1:0.0500 |
| | >20000 | 1000 | 5000 | 400 | <0.65 | 1:0.0800 |
| | >20000 | 1000 | 5000 | 500 | <0.75 | 1:0.1000 |
| | >20000 | 1000 | 5000 | 600 | <0.85 | 1:0.1200 |
| | >20000 | 1000 | 5000 | 800 | <1.05 | 1:0.1600 |
| | >20000 | 1000 | 2500 | 400 | <0.53 | 1:0.1600 |
| | >20000 | 1000 | 2500 | 600 | <0.73 | 1:0.2400 |
| | >20000 | 1000 | 2500 | 800 | <0.93 | 1:0.3200 |
| | >20000 | 1000 | 1750 | 400 | <0.49 | 1:0.2286 |
| | >20000 | 1000 | 1750 | 600 | <0.69 | 1:0.3429 |
| | >20000 | 1000 | 1750 | 800 | <0.89 | 1:0.4571 |
| | >20000 | 1000 | 875 | 500 | <0.54 | 1:0.5714 |
| | >20000 | 1000 | 875 | 600 | <0.64 | 1:0.6857 |
| | >20000 | 1000 | 875 | 800 | <0.84 | 1:0.9143 |
| | >20000 | 1000 | 437.5 | 800 | <0.82 | 1:1.8286 |

A: Surf. D
B: BNPD
Media: 1/10TSB
Inoculum size: 1.16E+08

PPM AI MIC Values (24 hrs)

| Test Organism | Alone CA | Alone CB | Combination Ca | Combination Cb | S.I. | Ratio (Ca:Cb) |
|---|---|---|---|---|---|---|
| Ps. aeruginosa ATCC# 15442 | >20000 | 10 | 875 | 8 | <0.84 | 1:0.0091 |
| | >20000 | 10 | 437.5 | 8 | <0.82 | 1:0.0183 |

A: Surf. D
B: BNPD
Media: 1/10TSB
Inoculum size: 1.808E+05

PPM AI MIC Values (24 hrs)

| Test Organism | Alone CA | Alone CB | Combination Ca | Combination Cb | S.I. | Ratio (Ca:Cb) |
|---|---|---|---|---|---|---|
| S. aureus ATCC# 6538 | >20000 | 20 | 20000 | 4 | <1.20 | 1:0.0002 |
| | >20000 | 20 | 10000 | 3 | <0.65 | 1:0.0003 |
| | >20000 | 20 | 10000 | 6 | <0.80 | 1:0.0006 |
| | >20000 | 20 | 10000 | 8 | <0.90 | 1:0.0008 |
| | >20000 | 20 | 10000 | 10 | <1.00 | 1:0.0010 |
| | >20000 | 20 | 5000 | 2 | <0.35 | 1:0.0004 |
| | >20000 | 20 | 5000 | 4 | <0.45 | 1:0.0008 |
| | >20000 | 20 | 5000 | 8 | <0.65 | 1:0.0016 |
| | >20000 | 20 | 5000 | 10 | <0.75 | 1:0.0020 |
| | >20000 | 20 | 5000 | 2 | <0.35 | 1:0.0004 |
| | >20000 | 20 | 5000 | 6 | <0.55 | 1:0.0012 |
| | >20000 | 20 | 5000 | 10 | <0.75 | 1:0.0020 |
| | >20000 | 20 | 1750 | 2 | <0.19 | 1:0.0011 |
| | >20000 | 20 | 1750 | 8 | <0.49 | 1:0.0046 |
| | >20000 | 20 | 1750 | 10 | <0.59 | 1:0.0057 |
| | >20000 | 20 | 875 | 2 | <0.14 | 1:0.0023 |

-continued

A: Surf. E
B: BNPD
Media: PDB
Inoculum size: 1.808E+06CFU/ml

| Test Organism | PPM AI MIC Values (24 hrs) | | | | | |
|---|---|---|---|---|---|---|
| | Alone | | Combination | | | |
| | CA | CB | Ca | Cb | S.I. | Ratio (Ca:Cb) |
| | >20000 | 20 | 875 | 4 | <0.24 | 1:0.0046 |
| | >20000 | 20 | 875 | 6 | <0.34 | 1:0.0069 |
| | >20000 | 20 | 875 | 10 | <0.54 | 1:0.0114 |
| | >20000 | 20 | 437.5 | 6 | <0.32 | 1:0.0137 |
| | >20000 | 20 | 437.5 | 8 | <0.42 | 1:0.0183 |
| | >20000 | 20 | 437.5 | 10 | <0.52 | 1:0.0229 |
| | >20000 | 20 | 218.75 | 8 | <0.41 | 1:0.0366 |
| | >20000 | 20 | 218.75 | 10 | <0.51 | 1:0.0457 |

A: Surf. E
B: BNPD
Media: PDB
Inoculum size: 1.808E+06CFU/ml

| Test Organism | PPM AI MIC Values (48 hrs) | | | | | Ratio |
|---|---|---|---|---|---|---|
| | Alone | | Combination | | | |
| | CA | CB | Ca | Cb | S.I. | (Ca:Cb) |
| C. albicans ATCC# 10203 | >20000 | 1000 | 20000 | 200 | <1.20 | 1:0.0100 |
| | >20000 | 1000 | 10000 | 200 | <0.70 | 1:0.0200 |
| | >20000 | 1000 | 10000 | 300 | <0.80 | 1:0.0300 |
| | >20000 | 1000 | 10000 | 500 | <1.00 | 1:0.0500 |
| | >20000 | 1000 | 5000 | 200 | <0.45 | 1:0.0400 |
| | >20000 | 1000 | 5000 | 400 | <0.65 | 1:0.0800 |
| | >20000 | 1000 | 5000 | 600 | <0.85 | 1:0.1200 |
| | >20000 | 1000 | 5000 | 800 | <1.05 | 1:0.1600 |
| | >20000 | 1000 | 2500 | 400 | <0.53 | 1:0.1600 |
| | >20000 | 1000 | 2500 | 600 | <0.73 | 1:0.2400 |
| | >20000 | 1000 | 2500 | 800 | <0.93 | 1:0.3200 |
| | >20000 | 1000 | 1750 | 500 | <0.59 | 1:0.2857 |
| | >20000 | 1000 | 1750 | 800 | <0.89 | 1:0.4571 |
| | >20000 | 1000 | 875 | 800 | <0.84 | 1:0.9143 |

A: Surf. E
B: BNPD
Media: 1/10TSB
Inoculum size: 5.727E+07CFU/ml

| Test Organism | PPM AI MIC Values (24 hrs) | | | | | |
|---|---|---|---|---|---|---|
| | Alone | | Combination | | | |
| | CA | CB | Ca | Cb | S.I. | Ratio (Ca:Cb) |
| Ps. aeruginosa ATCC# 15442 | >20000 | 10 | 5000 | 8 | <1.05 | 1:0.0016 |
| | >20000 | 10 | 2500 | 8 | <0.93 | 1:0.0032 |
| | >20000 | 10 | 1750 | 8 | <0.89 | 1:0.0046 |
| | >20000 | 10 | 875 | 8 | <0.84 | 1:0.0091 |
| | >20000 | 10 | 437.5 | 8 | <0.82 | 1:0.0183 |
| | >20000 | 10 | 218.75 | 8 | <0.81 | 1:0.0366 |

A: Surf. E
B: BNPD
Media: 1/10TSB
Inoculum size: 1.808E+06CFU/ml

| Test Organism | PPM AI MIC Values (24 hrs) | | | | | |
|---|---|---|---|---|---|---|
| | Alone | | Combination | | | |
| | CA | CB | Ca | Cb | S.I. | Ratio (Ca:Cb) |
| S. aureus ATCC# 6538 | >20000 | 20 | 20000 | 8 | <1.40 | 1:0.0004 |
| | >20000 | 20 | 10000 | 8 | <0.90 | 1:0.0008 |
| | >20000 | 20 | 5000 | 8 | <0.65 | 1:0.0016 |
| | >20000 | 20 | 5000 | 10 | <0.75 | 1:0.0020 |
| | >20000 | 20 | 2500 | 8 | <0.53 | 1:0.0032 |
| | >20000 | 20 | 2500 | 10 | <0.63 | 1:0.0040 |
| | >20000 | 20 | 1750 | 8 | <0.49 | 1:0.0046 |
| | >20000 | 20 | 1750 | 10 | <0.59 | 1:0.0057 |
| | >20000 | 20 | 875 | 8 | <0.44 | 1:0.0091 |
| | >20000 | 20 | 875 | 10 | <0.54 | 1:0.0114 |

No synergy: A. niger

A: Surf. A
B: DAZOMET
Media: 1/10 TSB
Inoculum size: 8.13E+07
S. aureus ATCC 6538 No Synergy A: Surf. A
B: DAZOMET
Media: PBD
Inoculum size: 1.156E+06

| Test Organism | PPM AI MIC Values (3rd day) | | | | | |
|---|---|---|---|---|---|---|
| | Alone | | Combination | | | |
| | CA | CB | Ca | Cb | S.I. | Ratio (Ca:Cb) |
| A. niger ATCC# 16404 | >20000 | 60 | 10000 | 0.6 | <0.51 | 1:0.0001 |
| | >20000 | 60 | 10000 | 0.8 | <0.51 | 1:0.0001 |
| | >20000 | 60 | 10000 | 1 | <0.52 | 1:0.0002 |
| | >20000 | 60 | 10000 | 2 | <0.53 | 1:0.0003 |
| | >20000 | 60 | 10000 | 3 | <0.55 | 1:0.0004 |
| | >20000 | 60 | 10000 | 4 | <0.57 | 1:0.0005 |
| | >20000 | 60 | 10000 | 5 | <0.58 | 1:0.0006 |
| | >20000 | 60 | 10000 | 6 | <0.60 | 1:0.0008 |
| | >20000 | 60 | 10000 | 8 | <0.63 | 1:0.0010 |
| | >20000 | 60 | 10000 | 10 | <0.67 | 1:0.0020 |
| | >20000 | 60 | 10000 | 20 | <0.83 | 1:0.0030 |
| | >20000 | 60 | 10000 | 30 | <1.00 | 1:0.0040 |
| | >20000 | 60 | 10000 | 40 | <1.17 | 1:0.0050 |
| | >20000 | 60 | 10000 | 50 | <1.33 | 1:0.0008 |
| | >20000 | 60 | 5000 | 4 | <0.32 | 1:0.0016 |
| | >20000 | 60 | 5000 | 8 | <0.38 | 1:0.0020 |
| | >20000 | 60 | 5000 | 10 | <0.42 | 1:0.0040 |
| | >20000 | 60 | 5000 | 20 | <0.58 | 1:0.0060 |
| | >20000 | 60 | 5000 | 30 | <0.75 | 1:0.0080 |
| | >20000 | 60 | 5000 | 40 | <0.92 | 1:0.0100 |
| | >20000 | 60 | 5000 | 50 | <1.08 | 1:0.0020 |
| | >20000 | 60 | 2500 | 5 | <0.21 | 1:0.0024 |
| | >20000 | 60 | 2500 | 6 | <0.23 | 1:0.0032 |
| | >20000 | 60 | 2500 | 8 | <0.26 | 1:0.0040 |
| | >20000 | 60 | 2500 | 10 | <0.29 | 1:0.0080 |
| | >20000 | 60 | 2500 | 20 | <0.46 | 1:0.0120 |
| | >20000 | 60 | 2500 | 30 | <0.63 | 1:0.0160 |
| | >20000 | 60 | 2500 | 40 | <0.79 | 1:0.0200 |
| | >20000 | 60 | 2500 | 50 | <0.96 | 1:0.0029 |
| | >20000 | 60 | 1750 | 5 | <0.17 | 1:0.0020 |
| | >20000 | 60 | 1750 | 6 | <0.23 | 1:0.0024 |
| | >20000 | 60 | 1750 | 8 | <0.26 | 1:0.0032 |
| | >20000 | 60 | 1750 | 10 | <0.29 | 1:0.0040 |
| | >20000 | 60 | 1750 | 20 | <0.46 | 1:0.0080 |

| | PPM AI MIC Values (3rd day) | | | | | |
|---|---|---|---|---|---|---|
| Test | Alone | | Combination | | | |
| Organism | CA | CB | Ca | Cb | S.I. | Ratio (Ca:Cb) |
| | >20000 | 60 | 1750 | 30 | <0.63 | 1:0.0120 |
| | >20000 | 60 | 1750 | 40 | <0.79 | 1:0.0160 |
| | >20000 | 60 | 1750 | 50 | <0.96 | 1:0.0200 |
| | >20000 | 60 | 875 | 20 | <0.17 | 1:0.0029 |
| | >20000 | 60 | 875 | 30 | <0.19 | 1:0.0034 |
| | >20000 | 60 | 875 | 40 | <0.22 | 1:0.0046 |
| | >20000 | 60 | 875 | 50 | <0.25 | 1:0.0057 |
| | >20000 | 60 | 437.5 | 30 | <0.42 | 1:0.0114 |
| | >20000 | 60 | 437.5 | 40 | <0.59 | 1:0.0171 |
| | >20000 | 60 | 437.5 | 50 | <0.75 | 1:0.0229 |
| | >20000 | 60 | 218.75 | 40 | <0.92 | 1:0.0286 |
| | >20000 | 60 | 218.75 | 50 | <0.38 | 1:0.0229 |

A: Surf. A
B: DAZOMET
Media: PBD
Inoculum size: 1.156E+06

| | PPM AI MIC Values (48 hrs) | | | | | |
|---|---|---|---|---|---|---|
| Test | Alone | | Combination | | | |
| Organism | CA | CB | Ca | Cb | S.I. | Ratio (Ca:Cb) |
| C. albicans ATCC# 10203 | >20000 | 50 | 2500 | 40 | <0.93 | 1:0.0160 |
| | >20000 | 50 | 1750 | 40 | <0.89 | 1:0.0229 |
| | >20000 | 50 | 437.5 | 40 | <0.82 | 1:0.0914 |
| | >20000 | 50 | 218.75 | 40 | <0.81 | 1:0.1829 |

A: Surf. A
B: DAZOMET
Media: 1/10TSB
Inoculum size: 8.134E+07

| | PPM AI MIC Values (24 hrs) | | | | | |
|---|---|---|---|---|---|---|
| Test | Alone | | Combination | | | |
| Organism | CA | CB | Ca | Cb | S.I. | Ratio (Ca:Cb) |
| Ps. aeruginosa ATCC# 15442 | >20000 | 80 | 2500 | 4 | <0.18 | 1:0.0016 |
| | >20000 | 80 | 2500 | 5 | <0.19 | 1:0.0020 |
| | >20000 | 80 | 2500 | 6 | <0.20 | 1:0.0024 |
| | >20000 | 80 | 2500 | 8 | <0.23 | 1:0.0032 |
| | >20000 | 80 | 2500 | 10 | <0.25 | 1:0.0040 |
| | >20000 | 80 | 2500 | 20 | <0.38 | 1:0.0080 |
| | >20000 | 80 | 2500 | 30 | <0.50 | 1:0.0120 |
| | >20000 | 80 | 2500 | 40 | <0.63 | 1:0.0160 |
| | >20000 | 80 | 2500 | 50 | <0.75 | 1:0.0200 |
| | >20000 | 80 | 2500 | 60 | <0.88 | 1:0.0240 |
| | >20000 | 80 | 1750 | 6 | <0.16 | 1:0.0034 |
| | >20000 | 80 | 1750 | 8 | <0.19 | 1:0.0046 |
| | >20000 | 80 | 1750 | 10 | <0.21 | 1:0.0057 |
| | >20000 | 80 | 1750 | 20 | <0.34 | 1:0.0114 |
| | >20000 | 80 | 1750 | 30 | <0.46 | 1:0.0171 |
| | >20000 | 80 | 1750 | 40 | <0.59 | 1:0.0229 |
| | >20000 | 80 | 1750 | 50 | <0.71 | 1:0.0286 |
| | >20000 | 80 | 1750 | 60 | <0.84 | 1:0.0343 |
| | >20000 | 80 | 437.5 | 60 | <0.77 | 1:0.1371 |
| | >20000 | 80 | 218.75 | 60 | <0.76 | 1:0.2743 |

A: Surf. E
B: DAZOMET
Media: PDB
Inoculum size: 1.156E+06
C. albicans ATCC 102031 No synergy
A: Surf. E
B: DAZOMET
Media: 1/10 TSB
Inoculum size: 5.7E+07
P. aeruginosa ATCC 15442 No synergy
A: Surf. E
B: DAZOMET
Media: 1/10TSB
Inoculum size: 1.8E+06

| | PPM AI MIC Values (24 hrs) | | | | | |
|---|---|---|---|---|---|---|
| Test | Alone | | Combination | | | |
| Organism | CA | CB | Ca | Cb | S.I. | Ratio (Ca:Cb) |
| S. aureus ATCC# 6538 | >20000 | 200 | 437.5 | 100 | <0.52 | 1:0.2286 |

A: Surf. E
B: DAZOMET
Media: PBD
Inoculum size: 1.156E+06

| | PPM AI MIC Values (3rd day) | | | | | |
|---|---|---|---|---|---|---|
| Test | Alone | | Combination | | | |
| Organism | CA | CB | Ca | Cb | S.I. | Ratio (Ca:Cb) |
| A. niger ATCC# 16404 | >20000 | 30 | 10000 | 2 | <0.57 | 1:0.0002 |
| | >20000 | 30 | 10000 | 4 | <0.63 | 1:0.0004 |
| | >20000 | 30 | 10000 | 6 | <0.70 | 1:0.0006 |
| | >20000 | 30 | 10000 | 8 | <0.77 | 1:0.0008 |
| | >20000 | 30 | 10000 | 10 | <0.83 | 1:0.0010 |
| | >20000 | 30 | 10000 | 20 | <1.17 | 1:0.0020 |
| | >20000 | 30 | 5000 | 0.4 | <0.26 | 1:0.0001 |
| | >20000 | 30 | 5000 | 0.5 | <0.27 | 1:0.0001 |
| | >20000 | 30 | 5000 | 0.6 | <0.27 | 1:0.0001 |
| | >20000 | 30 | 5000 | 0.8 | <0.28 | 1:0.0002 |
| | >20000 | 30 | 5000 | 1 | <0.28 | 1:0.0002 |
| | >20000 | 30 | 5000 | 2 | <0.32 | 1:0.0004 |
| | >20000 | 30 | 5000 | 3 | <0.35 | 1:0.0006 |
| | >20000 | 30 | 5000 | 4 | <0.38 | 1:0.0008 |
| | >20000 | 30 | 5000 | 5 | <0.42 | 1:0.0010 |
| | >20000 | 30 | 5000 | 6 | <0.45 | 1:0.0012 |
| | >20000 | 30 | 5000 | 8 | <0.52 | 1:0.0016 |
| | >20000 | 30 | 5000 | 10 | <0.58 | 1:0.0020 |
| | >20000 | 30 | 5000 | 20 | <0.92 | 1:0.0040 |
| | >20000 | 30 | 1750 | 0.4 | <0.10 | 1:0.0002 |
| | >20000 | 30 | 1750 | 0.5 | <0.10 | 1:0.0003 |
| | >20000 | 30 | 1750 | 0.6 | <0.11 | 1:0.0003 |
| | >20000 | 30 | 1750 | 0.8 | <0.11 | 1:0.0005 |
| | >20000 | 30 | 1750 | 1 | <0.12 | 1:0.0006 |
| | >20000 | 30 | 1750 | 2 | <0.15 | 1:0.0011 |
| | >20000 | 30 | 1750 | 3 | <0.19 | 1:0.0017 |
| | >20000 | 30 | 1750 | 4 | <0.22 | 1:0.0023 |
| | >20000 | 30 | 1750 | 5 | <0.25 | 1:0.0029 |
| | >20000 | 30 | 1750 | 6 | <0.29 | 1:0.0034 |
| | >20000 | 30 | 1750 | 8 | <0.35 | 1:0.0046 |
| | >20000 | 30 | 1750 | 10 | <0.42 | 1:0.0057 |
| | >20000 | 30 | 1750 | 20 | <0.75 | 1:0.0114 |
| | >20000 | 30 | 875 | 3 | <0.14 | 1:0.0034 |
| | >20000 | 30 | 875 | 4 | <0.18 | 1:0.0046 |
| | >20000 | 30 | 875 | 5 | <0.21 | 1:0.0057 |
| | >20000 | 30 | 875 | 6 | <0.24 | 1:0.0069 |
| | >20000 | 30 | 875 | 8 | <0.31 | 1:0.0091 |
| | >20000 | 30 | 875 | 10 | <0.38 | 1:0.0114 |

PPM AI MIC Values (3rd day)

| Test Organism | Alone CA | Alone CB | Combination Ca | Combination Cb | S.I. | Ratio (Ca:Cb) |
|---|---|---|---|---|---|---|
| | >20000 | 30 | 875 | 20 | <0.71 | 1:0.0229 |
| | >20000 | 30 | 437.5 | 0.2 | <0.03 | 1:0.0005 |
| | >20000 | 30 | 437.5 | 0.3 | <0.03 | 1:0.0007 |
| | >20000 | 30 | 437.5 | 0.4 | <0.04 | 1:0.0009 |
| | >20000 | 30 | 437.5 | 0.5 | <0.04 | 1:0.0011 |
| | >20000 | 30 | 437.5 | 0.6 | <0.04 | 1:0.0014 |
| | >20000 | 30 | 437.5 | 0.8 | <0.05 | 1:0.0018 |
| | >20000 | 30 | 437.5 | 1 | <0.06 | 1:0.0023 |
| | >20000 | 30 | 437.5 | 2 | <0.09 | 1:0.0046 |
| | >20000 | 30 | 437.5 | 3 | <0.12 | 1:0.0069 |
| | >20000 | 30 | 437.5 | 4 | <0.16 | 1:0.0091 |
| | >20000 | 30 | 437.5 | 5 | <0.19 | 1:0.0114 |
| | >20000 | 30 | 437.5 | 6 | <0.22 | 1:0.0137 |
| | >20000 | 30 | 437.5 | 8 | <0.29 | 1:0.0183 |
| | >20000 | 30 | 437.5 | 10 | <0.36 | 1:0.0229 |
| | >20000 | 30 | 437.5 | 20 | <0.69 | 1:0.0457 |
| | >20000 | 30 | 218.75 | 5 | <0.18 | 1:0.0229 |
| | >20000 | 30 | 218.75 | 6 | <0.21 | 1:0.0274 |
| | >20000 | 30 | 218.75 | 8 | <0.28 | 1:0.0366 |
| | >20000 | 30 | 218.75 | 10 | <<0.34 | 1:0.0457 |
| | >20000 | 30 | 218.75 | 20 | <0.68 | 1:0.0914 |

A: Surf. D
B: DAZOMET
Media: PDB
Inoculum size: 1.16E+08

*P. aeruginosa* ATCC 15442 No synergy

A: Surf. D
B: DAZOMET
Media: PBD
Inoculum size: 5.72E+05

PPM AI MIC Values (48 hrs)

| Test Organism | Alone CA | Alone CB | Combination Ca | Combination Cb | S.I. | Ratio (Ca:Cb) |
|---|---|---|---|---|---|---|
| *C. albicans* ATCC# 10203 | >20000 | 50 | 10000 | 10 | <0.70 | 1:0.0010 |
| | >20000 | 50 | 10000 | 20 | <0.90 | 1:0.0020 |
| | >20000 | 50 | 10000 | 30 | <1.10 | 1:0.0030 |
| | >20000 | 50 | 10000 | 40 | <1.30 | 1:0.0040 |
| | >20000 | 50 | 5000 | 30 | <0.85 | 1:0.0060 |
| | >20000 | 50 | 5000 | 40 | <1.05 | 1:0.0080 |
| | >20000 | 50 | 2500 | 5 | <0.23 | 1:0.0020 |
| | >20000 | 50 | 2500 | 10 | <0.33 | 1:0.0040 |
| | >20000 | 50 | 2500 | 20 | <0.53 | 1:0.0080 |
| | >20000 | 50 | 2500 | 30 | <0.73 | 1:0.0120 |
| | >20000 | 50 | 2500 | 40 | <0.93 | 1:0.0160 |
| | >20000 | 50 | 1750 | 6 | <0.21 | 1:0.0034 |
| | >20000 | 50 | 1750 | 10 | <0.29 | 1:0.0057 |
| | >20000 | 50 | 1750 | 20 | <0.49 | 1:0.0114 |
| | >20000 | 50 | 1750 | 30 | <0.69 | 1:0.0171 |
| | >20000 | 50 | 1750 | 40 | <0.89 | 1:0.0229 |
| | >20000 | 50 | 875 | 30 | <0.64 | 1:0.0343 |
| | >20000 | 50 | 875 | 40 | <0.84 | 1:0.0457 |
| | >20000 | 50 | 437.5 | 40 | <0.82 | 1:0.0914 |
| | >20000 | 50 | 218.75 | 40 | <0.81 | 1:0.1829 |

A: Surf. D
B: DAZOMET
Media: PBD
Inoculum size: 1.56E+06

PPM AI MIC Values (3rd day)

| Test Organism | Alone CA | Alone CB | Combination Ca | Combination Cb | S.I. | Ratio (Ca:Cb) |
|---|---|---|---|---|---|---|
| *A. niger* ATCC# 16404 | >20000 | 40 | 10000 | 0.2 | <0.51 | 1:0.0002 |
| | >20000 | 40 | 10000 | 0.3 | <0.51 | 1:0.0003 |
| | >20000 | 40 | 10000 | 0.4 | <0.51 | 1:0.0004 |
| | >20000 | 40 | 10000 | 0.5 | <0.51 | 1:0.0005 |
| | >20000 | 40 | 10000 | 0.6 | <0.52 | 1:0.0006 |
| | >20000 | 40 | 10000 | 0.8 | <0.52 | 1:0.0008 |
| | >20000 | 40 | 10000 | 1 | <0.53 | 1:0.0010 |
| | >20000 | 40 | 10000 | 2 | <0.55 | 1:0.0020 |
| | >20000 | 40 | 10000 | 3 | <0.58 | 1:0.0030 |
| | >20000 | 40 | 10000 | 4 | <0.60 | 1:0.0020 |
| | >20000 | 40 | 10000 | 5 | <0.63 | 1:0.0030 |
| | >20000 | 40 | 10000 | 6 | <0.65 | 1:0.0000 |
| | >20000 | 40 | 10000 | 8 | <0.70 | 1:0.0008 |
| | >20000 | 40 | 10000 | 10 | <0.75 | 1:0.0001 |
| | >20000 | 40 | 10000 | 20 | <1.00 | 1:0.0001 |
| | >20000 | 40 | 5000 | 0.2 | <0.26 | 1:0.0037 |
| | >20000 | 40 | 5000 | 0.3 | <0.26 | 1:0.0046 |
| | >20000 | 40 | 5000 | 0.4 | <0.26 | 1:0.0000 |
| | >20000 | 40 | 5000 | 0.5 | <0.26 | 1:0.0001 |
| | >20000 | 40 | 5000 | 0.6 | <0.27 | 1:0.0001 |
| | >20000 | 40 | 5000 | 0.8 | <0.27 | 1:0.0002 |
| | >20000 | 40 | 5000 | 1 | <0.28 | 1:0.0002 |
| | >20000 | 40 | 5000 | 2 | <0.30 | 1:0.0004 |
| | >20000 | 40 | 5000 | 3 | <0.33 | 1:0.0006 |
| | >20000 | 40 | 5000 | 4 | <0.35 | 1:0.0008 |
| | >20000 | 40 | 5000 | 5 | <0.38 | 1:0.0003 |
| | >20000 | 40 | 5000 | 6 | <0.40 | 1:0.0010 |
| | >20000 | 40 | 5000 | 8 | <0.45 | 1:0.0020 |
| | >20000 | 40 | 5000 | 10 | <0.50 | 1:0.0030 |
| | >20000 | 40 | 5000 | 20 | <0.75 | 1:0.0060 |
| | >20000 | 40 | 5000 | 30 | <1.00 | 1:0.0020 |
| | >20000 | 40 | 2500 | 0.2 | <0.13 | 1:0.0001 |
| | >20000 | 40 | 2500 | 0.3 | <0.13 | 1:0.0001 |
| | >20000 | 40 | 2500 | 0.4 | <0.14 | 1:0.0002 |
| | >20000 | 40 | 2500 | 0.5 | <0.14 | 1:0.0002 |
| | >20000 | 40 | 2500 | 0.6 | <0.14 | 1:0.0002 |
| | >20000 | 40 | 2500 | 0.8 | <0.15 | 1:0.0003 |
| | >20000 | 40 | 2500 | 1 | <0.15 | 1:0.0004 |
| | >20000 | 40 | 2500 | 2 | <0.18 | 1:0.0008 |
| | >20000 | 40 | 2500 | 3 | <0.20 | 1:0.0012 |
| | >20000 | 40 | 2500 | 4 | <0.23 | 1:0.0016 |
| | >20000 | 40 | 2500 | 5 | <0.25 | 1:0.0020 |
| | >20000 | 40 | 2500 | 6 | <0.28 | 1:0.0024 |
| | >20000 | 40 | 2500 | 8 | <0.33 | 1:0.0032 |
| | >20000 | 40 | 2500 | 10 | <0.38 | 1:0.0040 |
| | >20000 | 40 | 2500 | 20 | <0.63 | 1:0.0080 |
| | >20000 | 40 | 2500 | 30 | <0.88 | 1:0.0120 |
| | >20000 | 40 | 1750 | 0.2 | <0.09 | 1:0.0001 |
| | >20000 | 40 | 1750 | 0.3 | <0.10 | 1:0.0002 |
| | >20000 | 40 | 1750 | 0.4 | <0.10 | 1:0.0002 |
| | >20000 | 40 | 1750 | 0.5 | <0.10 | 1:0.0003 |
| | >20000 | 40 | 1750 | 0.6 | <0.10 | 1:0.0003 |
| | >20000 | 40 | 1750 | 0.8 | <0.11 | 1:0.0005 |
| | >20000 | 40 | 1750 | 1 | <0.11 | 1:0.0006 |
| | >20000 | 40 | 1750 | 2 | <0.14 | 1:0.0011 |
| | >20000 | 40 | 1750 | 3 | <0.16 | 1:0.0017 |
| | >20000 | 40 | 1750 | 4 | <0.19 | 1:0.0023 |
| | >20000 | 40 | 1750 | 5 | <0.21 | 1:0.0029 |
| | >20000 | 40 | 1750 | 6 | <0.24 | 1:0.0034 |
| | >20000 | 40 | 1750 | 8 | <0.29 | 1:0.0046 |
| | >20000 | 40 | 1750 | 10 | <0.34 | 1:0.0057 |
| | >20000 | 40 | 1750 | 20 | <0.59 | 1:0.0114 |
| | >20000 | 40 | 875 | 0.2 | <0.05 | 1:0.0002 |
| | >20000 | 40 | 875 | 0.3 | <0.05 | 1:0.0003 |
| | >20000 | 40 | 875 | 0.2 | <0.05 | 1:0.0002 |
| | >20000 | 40 | 875 | 0.4 | <0.05 | 1:0.0005 |
| | >20000 | 40 | 875 | 0.5 | <0.06 | 1:0.0006 |
| | >20000 | 40 | 875 | 0.6 | <0.06 | 1:0.0007 |
| | >20000 | 40 | 875 | 0.8 | <0.06 | 1:0.0009 |

PPM AI MIC Values (3rd day)

| Test Organism | Alone CA | Alone CB | Combination Ca | Combination Cb | S.I. | Ratio (Ca:Cb) |
|---|---|---|---|---|---|---|
| | >20000 | 40 | 875 | 1 | <0.07 | 1:0.0011 |
| | >20000 | 40 | 875 | 2 | <0.09 | 1:0.0023 |
| | >20000 | 40 | 875 | 0.2 | <0.05 | 1:0.0002 |
| | >20000 | 40 | 875 | 0.3 | <0.05 | 1:0.0003 |
| | >20000 | 40 | 875 | 0.4 | <0.05 | 1:0.0005 |
| | >20000 | 40 | 875 | 0.5 | <0.06 | 1:0.0006 |
| | >20000 | 40 | 875 | 0.6 | <0.06 | 1:0.0007 |
| | >20000 | 40 | 875 | 0.8 | <0.06 | 1:0.0009 |
| | >20000 | 40 | 875 | 1 | <0.07 | 1:0.0011 |
| | >20000 | 40 | 875 | 2 | <0.09 | 1:0.0023 |
| | >20000 | 40 | 875 | 3 | <0.12 | 1:0.0034 |
| | >20000 | 40 | 875 | 4 | <0.14 | 1:0.0046 |
| | >20000 | 40 | 875 | 5 | <0.17 | 1:0.0057 |
| | >20000 | 40 | 875 | 6 | <0.19 | 1:0.0069 |
| | >20000 | 40 | 875 | 8 | <0.24 | 1:0.0091 |
| | >20000 | 40 | 875 | 10 | <0.29 | 1:0.0114 |
| | >20000 | 40 | 875 | 20 | <0.54 | 1:0.0229 |
| | >20000 | 40 | 437.5 | 0.4 | <0.03 | 1:0.0009 |
| | >20000 | 40 | 437.5 | 0.5 | <0.03 | 1:0.0011 |
| | >20000 | 40 | 437.5 | 0.6 | <0.04 | 1:0.0014 |
| | >20000 | 40 | 437.5 | 0.8 | <0.04 | 1:0.0018 |
| | >20000 | 40 | 437.5 | 0.4 | <0.03 | 1:0.0009 |
| | >20000 | 40 | 437.5 | 1 | <0.05 | 1:0.0023 |
| | >20000 | 40 | 437.5 | 2 | <0.07 | 1:0.0046 |
| | >20000 | 40 | 437.5 | 3 | <0.10 | 1:0.0069 |
| | >20000 | 40 | 437.5 | 4 | <0.12 | 1:0.0091 |
| | >20000 | 40 | 437.5 | 5 | <0.15 | 1:0.0114 |
| | >20000 | 40 | 437.5 | 6 | <0.17 | 1:0.0137 |
| | >20000 | 40 | 437.5 | 8 | <0.22 | 1:0.0183 |
| | >20000 | 40 | 437.5 | 10 | <0.27 | 1:0.0229 |
| | >20000 | 40 | 437.5 | 20 | <0.52 | 1:0.0457 |
| | >20000 | 40 | 218.75 | 0.6 | <0.03 | 1:0.0027 |
| | >20000 | 40 | 218.75 | 0.8 | <0.03 | 1:0.0037 |
| | >20000 | 40 | 218.75 | 1 | <0.04 | 1:0.0046 |
| | >20000 | 40 | 218.75 | 2 | <0.06 | 1:0.0091 |
| | >20000 | 40 | 218.75 | 3 | <0.09 | 1:0.0137 |
| | >20000 | 40 | 218.75 | 4 | <0.11 | 1:0.0183 |
| | >20000 | 40 | 218.75 | 5 | <0.14 | 1:0.0229 |
| | >20000 | 40 | 218.75 | 6 | <0.16 | 1:0.0274 |
| | >20000 | 40 | 218.75 | 8 | <0.21 | 1:0.0366 |
| | >20000 | 40 | 218.75 | 10 | <0.26 | 1:0.0457 |
| | >20000 | 40 | 218.75 | 20 | <0.51 | 1:0.0914 |
| | >20000 | 40 | 20000 | 0.2 | <1.01 | 1:0.0000 |

A: Surf. D
B: DAZOMET
Media: 1/10TSB
Inoculum size: 5.72E+05

PPM AI MIC Values (24 hrs)

| Test Organism | Alone CA | Alone CB | Combination Ca | Combination Cb | S.I. | Ratio (Ca:Cb) |
|---|---|---|---|---|---|---|
| S. aureus ATCC# 6538 | >20000 | 200 | 10000 | 20 | 0.60 | 1:0.0020 |
| | >20000 | 200 | 10000 | 30 | 0.65 | 1:0.0030 |
| | >20000 | 200 | 10000 | 40 | 0.70 | 1:0.0040 |
| | >20000 | 200 | 10000 | 50 | 0.75 | 1:0.0050 |
| | >20000 | 200 | 10000 | 60 | 0.80 | 1:0.0060 |
| | >20000 | 200 | 10000 | 80 | 0.90 | 1:0.0080 |
| | >20000 | 200 | 10000 | 100 | 1.00 | 1:0.0100 |
| | >20000 | 200 | 10000 | 20 | 0.60 | 1:0.0020 |
| | >20000 | 200 | 5000 | 4 | 0.27 | 1:0.0008 |
| | >20000 | 200 | 5000 | 5 | 0.28 | 1:0.0010 |
| | >20000 | 200 | 5000 | 6 | 0.28 | 1:0.0012 |
| | >20000 | 200 | 5000 | 8 | 0.29 | 1:0.0016 |
| | >20000 | 200 | 5000 | 10 | 0.30 | 1:0.0020 |
| | >20000 | 200 | 5000 | 20 | 0.35 | 1:0.0040 |
| | >20000 | 200 | 5000 | 30 | 0.40 | 1:0.0060 |
| | >20000 | 200 | 5000 | 8 | 0.29 | 1:0.0016 |
| | >20000 | 200 | 5000 | 10 | 0.30 | 1:0.0020 |
| | >20000 | 200 | 5000 | 20 | 0.35 | 1:0.0040 |
| | >20000 | 200 | 5000 | 30 | 0.40 | 1:0.0060 |
| | >20000 | 200 | 5000 | 40 | 0.45 | 1:0.0080 |
| | >20000 | 200 | 5000 | 50 | 0.50 | 1:0.0100 |
| | >20000 | 200 | 5000 | 60 | 0.55 | 1:0.0120 |
| | >20000 | 200 | 5000 | 80 | 0.65 | 1:0.0160 |
| | >20000 | 200 | 5000 | 100 | 0.75 | 1:0.0200 |
| | >20000 | 200 | 2500 | 20 | 0.23 | 1:0.0080 |
| | >20000 | 200 | 2500 | 30 | 0.28 | 1:0.0120 |
| | >20000 | 200 | 2500 | 40 | 0.33 | 1:0.0160 |
| | >20000 | 200 | 2500 | 50 | 0.38 | 1:0.0200 |
| | >20000 | 200 | 2500 | 60 | 0.43 | 1:0.0240 |
| | >20000 | 200 | 2500 | 80 | 0.53 | 1:0.0320 |
| | >20000 | 200 | 2500 | 100 | 0.63 | 1:0.0400 |
| | >20000 | 200 | 1750 | 0.2 | 0.09 | 1:0.0001 |
| | >20000 | 200 | 1750 | 0.3 | 0.09 | 1:0.0002 |
| | >20000 | 200 | 1750 | 0.4 | 0.09 | 1:0.0002 |
| | >20000 | 200 | 1750 | 0.5 | 0.09 | 1:0.0003 |
| | >20000 | 200 | 1750 | 0.6 | 0.09 | 1:0.0003 |
| | >20000 | 200 | 1750 | 0.8 | 0.09 | 1:0.0005 |
| | >20000 | 200 | 1750 | 1 | 0.09 | 1:0.0006 |
| | >20000 | 200 | 1750 | 2 | 0.10 | 1:0.0011 |
| | >20000 | 200 | 1750 | 3 | 0.10 | 1:0.0017 |
| | >20000 | 200 | 1750 | 4 | 0.11 | 1:0.0023 |
| | >20000 | 200 | 1750 | 5 | 0.11 | 1:0.0029 |
| | >20000 | 200 | 1750 | 6 | 0.12 | 1:0.0034 |
| | >20000 | 200 | 1750 | 8 | 0.13 | 1:0.0046 |
| | >20000 | 200 | 1750 | 10 | 0.14 | 1:0.0057 |
| | >20000 | 200 | 1750 | 20 | 0.19 | 1:0.0114 |
| | >20000 | 200 | 1750 | 40 | 0.29 | 1:0.0229 |
| | >20000 | 200 | 1750 | 60 | 0.39 | 1:0.0343 |
| | >20000 | 200 | 1750 | 80 | 0.49 | 1:0.0457 |
| | >20000 | 200 | 1750 | 100 | 0.59 | 1:0.0571 |
| | >20000 | 200 | 875 | 0.2 | 0.04 | 1:0.0002 |
| | >20000 | 200 | 875 | 0.3 | 0.05 | 1:0.0003 |
| | >20000 | 200 | 875 | 0.4 | 0.05 | 1:0.0005 |
| | >20000 | 200 | 875 | 0.5 | 0.05 | 1:0.0006 |
| | >20000 | 200 | 875 | 0.6 | 0.05 | 1:0.0007 |
| | >20000 | 200 | 875 | 0.8 | 0.05 | 1:0.0009 |
| | >20000 | 200 | 875 | 1 | 0.05 | 1:0.0011 |
| | >20000 | 200 | 875 | 2 | 0.05 | 1:0.0023 |
| | >20000 | 200 | 875 | 3 | 0.06 | 1:0.0034 |
| | >20000 | 200 | 875 | 4 | 0.06 | 1:0.0046 |
| | >20000 | 200 | 875 | 5 | 0.07 | 1:0.0057 |
| | >20000 | 200 | 875 | 6 | 0.07 | 1:0.0069 |
| | >20000 | 200 | 875 | 8 | 0.08 | 1:0.0091 |
| | >20000 | 200 | 875 | 10 | 0.09 | 1:0.0114 |
| | >20000 | 200 | 875 | 20 | 0.14 | 1:0.0229 |
| | >20000 | 200 | 875 | 30 | 0.19 | 1:0.0343 |
| | >20000 | 200 | 875 | 40 | 0.24 | 1:0.0457 |
| | >20000 | 200 | 875 | 50 | 0.29 | 1:0.0571 |
| | >20000 | 200 | 875 | 60 | 0.34 | 1:0.0686 |
| | >20000 | 200 | 875 | 80 | 0.44 | 1:0.0914 |
| | >20000 | 200 | 875 | 100 | 0.54 | 1:0.1143 |
| | >20000 | 200 | 437.5 | 30 | 0.17 | 1:0.0686 |
| | >20000 | 200 | 437.5 | 40 | 0.22 | 1:0.0914 |
| | >20000 | 200 | 437.5 | 50 | 0.27 | 1:0.1143 |
| | >20000 | 200 | 437.5 | 60 | 0.32 | 1:0.1371 |
| | >20000 | 200 | 437.5 | 80 | 0.42 | 1:0.1829 |
| | >20000 | 200 | 437.5 | 100 | 0.52 | 1:0.2286 |
| | >20000 | 200 | 218.75 | 50 | 0.26 | 1:0.2286 |
| | >20000 | 200 | 218.75 | 60 | 0.31 | 1:0.2743 |
| | >20000 | 200 | 218.75 | 80 | 0.41 | 1:0.3657 |
| | >20000 | 200 | 218.75 | 100 | 0.51 | 1:0.4571 |

A: Surf. A
B: BIOBAN P-1487
Media: PDB
Inoculum size: 1.156E+06CFU/ml

| Test Organism | PPM AI MIC Values (3rd day) Alone | | Combination | | | |
|---|---|---|---|---|---|---|
| | CA | CB | Ca | Cb | S.I. | Ratio (Ca:Cb) |
| A. niger ATCC# 16404 | >20000 | 80 | 20000 | 5 | <1.06 | 1:0.0003 |
| | >20000 | 80 | 10000 | 6 | <0.58 | 1:0.0006 |
| | >20000 | 80 | 10000 | 10 | <0.63 | 1:0.0010 |
| | >20000 | 80 | 10000 | 20 | <0.75 | 1:0.0020 |
| | >20000 | 80 | 10000 | 40 | <1.00 | 1:0.0040 |
| | >20000 | 80 | 5000 | 30 | <0.63 | 1:0.0060 |
| | >20000 | 80 | 5000 | 40 | <0.75 | 1:0.0080 |
| | >20000 | 80 | 5000 | 60 | <1.00 | 1:0.0120 |
| | >20000 | 80 | 2500 | 30 | <0.50 | 1:0.0120 |
| | >20000 | 80 | 2500 | 40 | <0.63 | 1:0.0160 |
| | >20000 | 80 | 2500 | 60 | <0.88 | 1:0.0240 |
| | >20000 | 80 | 1750 | 30 | <0.46 | 1:0.0171 |
| | >20000 | 80 | 1750 | 40 | <0.59 | 1:0.0229 |
| | >20000 | 80 | 1750 | 60 | <0.84 | 1:0.0343 |
| | >20000 | 80 | 875 | 30 | <0.42 | 1:0.0343 |
| | >20000 | 80 | 875 | 60 | <0.79 | 1:0.0686 |
| | >20000 | 80 | 437.5 | 50 | <0.65 | 1:0.1143 |
| | >20000 | 80 | 437.5 | 60 | <0.77 | 1:0.1371 |
| | >20000 | 80 | 218.75 | 50 | <0.64 | 1:0.2286 |
| | >20000 | 80 | 218.75 | 60 | <0.76 | 1:0.2743 |

A: Surf. A
B: BIOBAN P-1487
Media: PBD
Inoculum size: 1.156E+06CFU/ml

| Test Organism | PPM AI MIC Values (48 hrs) Alone | | Combination | | | |
|---|---|---|---|---|---|---|
| | CA | CB | Ca | Cb | S.I. | Ratio (Ca:Cb) |
| C. albicans ATCC# 10231 | >20000 | 30 | 20000 | 10 | <1.33 | 1:0.0005 |
| | >20000 | 30 | 10000 | 10 | <0.83 | 1:0.0010 |
| | >20000 | 30 | 2500 | 8 | <0.39 | 1:0.0032 |
| | >20000 | 30 | 2500 | 10 | <0.46 | 1:0.0040 |
| | >20000 | 30 | 2500 | 20 | <0.79 | 1:0.0080 |
| | >20000 | 30 | 1750 | 10 | <0.42 | 1:0.0057 |
| | >20000 | 30 | 1750 | 20 | <0.75 | 1:0.0114 |
| | >20000 | 30 | 437.5 | 20 | <0.69 | 1:0.0457 |
| | >20000 | 30 | 218.75 | 20 | <0.68 | 1:0.0914 |

A: Surf. A
B: BIOBAN P-1487
Media: 1/10TSB
Inoculum size: 8.134E+07CFU/ml

| Test Organism | PPM AI MIC Values (24 hrs) Alone | | Combination | | | |
|---|---|---|---|---|---|---|
| | CA | CB | Ca | Cb | S.I. | Ratio (Ca:Cb) |
| Ps. aeruginosa ATCC# 15442 | >20000 | 80 | 20000 | 60 | <1.75 | 1:0.0030 |
| | >20000 | 80 | 5000 | 60 | <1.00 | 1:0.0120 |
| | >20000 | 80 | 2500 | 40 | <0.63 | 1:0.0160 |
| | >20000 | 80 | 2500 | 60 | <0.88 | 1:0.0240 |
| | >20000 | 80 | 1750 | 50 | <0.71 | 1:0.0286 |
| | >20000 | 80 | 1750 | 60 | <0.84 | 1:0.0343 |
| | >20000 | 80 | 875 | 50 | <0.67 | 1:0.0571 |
| | >20000 | 80 | 875 | 60 | <0.79 | 1:0.0686 |
| | >20000 | 80 | 437.5 | 40 | <0.52 | 1:0.0914 |
| | >20000 | 80 | 437.5 | 60 | <0.77 | 1:0.1371 |
| | >20000 | 80 | 218.75 | 60 | <0.76 | 1:0.2743 |

No Synergy: S. aureus

A: Surf. E
B: BIOBAN P-1487
Media: PBD
Inoculum size: 1.156E+06CFU/ml

| Test Organism | PPM AI MIC Values (3rd day) Alone | | Combination | | | |
|---|---|---|---|---|---|---|
| | CA | CB | Ca | Cb | S.I. | Ratio (Ca:Cb) |
| A. niger ATCC# 16404 | >20000 | 60 | 20000 | 30 | <1.50 | 1:0.0015 |
| | >20000 | 60 | 10000 | 30 | <1.00 | 1:0.0030 |
| | >20000 | 60 | 5000 | 30 | <0.75 | 1:0.0060 |
| | >20000 | 60 | 5000 | 40 | <0.92 | 1:0.0080 |
| | >20000 | 60 | 5000 | 50 | <1.08 | 1:0.0100 |
| | >20000 | 60 | 2500 | 30 | <0.63 | 1:0.0120 |
| | >20000 | 60 | 2500 | 40 | <0.79 | 1:0.0160 |
| | >20000 | 60 | 2500 | 50 | <0.96 | 1:0.0200 |
| | >20000 | 60 | 1750 | 30 | <0.59 | 1:0.0171 |
| | >20000 | 60 | 1750 | 40 | <0.75 | 1:0.0229 |
| | >20000 | 60 | 1750 | 50 | <0.92 | 1:0.0286 |
| | >20000 | 60 | 875 | 30 | <0.54 | 1:0.0343 |
| | >20000 | 60 | 875 | 40 | <0.71 | 1:0.0457 |
| | >20000 | 60 | 875 | 50 | <0.88 | 1:0.0571 |
| | >20000 | 60 | 437.5 | 30 | <0.52 | 1:0.0686 |
| | >20000 | 60 | 437.5 | 40 | <0.69 | 1:0.0914 |
| | >20000 | 60 | 437.5 | 50 | <0.86 | 1:0.1143 |
| | >20000 | 60 | 218.75 | 30 | <0.51 | 1:0.1371 |
| | >20000 | 60 | 218.75 | 40 | <0.68 | 1:0.1829 |
| | >20000 | 60 | 218.75 | 50 | <0.84 | 1:0.2286 |

A: Surf. E
B: BIOBAN P-1487
Media: PDB
Inoculum size: 1.808E+06

| Test Organism | PPM AI MIC Values (48 hrs) Alone | | Combination | | | |
|---|---|---|---|---|---|---|
| | CA | CB | Ca | Cb | S.I. | Ratio (Ca:Cb) |
| C. albicans ATCC# 10203 | >20000 | 30 | 20000 | 0.04 | <1.00 | 1:0.0000 |
| | >20000 | 30 | 10000 | 0.04 | <0.50 | 1:0.0000 |
| | >20000 | 30 | 10000 | 0.4 | <0.51 | 1:0.0000 |
| | >20000 | 30 | 10000 | 4 | <0.63 | 1:0.0004 |
| | >20000 | 30 | 10000 | 10 | <0.83 | 1:0.0010 |
| | >20000 | 30 | 10000 | 20 | <1.17 | 1:0.0020 |
| | >20000 | 30 | 5000 | 4 | <0.38 | 1:0.0008 |
| | >20000 | 30 | 5000 | 5 | <0.42 | 1:0.0010 |
| | >20000 | 30 | 5000 | 10 | <0.58 | 1:0.0020 |
| | >20000 | 30 | 5000 | 20 | <0.92 | 1:0.0040 |
| | >20000 | 30 | 2500 | 4 | <0.26 | 1:0.0016 |
| | >20000 | 30 | 2500 | 10 | <0.46 | 1:0.0040 |
| | >20000 | 30 | 2500 | 20 | <0.79 | 1:0.0080 |
| | >20000 | 30 | 1750 | 5 | <0.25 | 1:0.0029 |
| | >20000 | 30 | 1750 | 10 | <0.42 | 1:0.0057 |
| | >20000 | 30 | 1750 | 20 | <0.75 | 1:0.0114 |
| | >20000 | 30 | 875 | 8 | <0.31 | 1:0.0091 |
| | >20000 | 30 | 875 | 10 | <0.38 | 1:0.0114 |
| | >20000 | 30 | 875 | 20 | <0.71 | 1:0.0229 |
| | >20000 | 30 | 437.5 | 8 | <0.29 | 1:0.0183 |

| | PPM AI MIC Values (48 hrs) | | | | | |
|---|---|---|---|---|---|---|
| Test | Alone | | Combination | | | |
| Organism | CA | CB | Ca | Cb | S.I. | Ratio (Ca:Cb) |
| | >20000 | 30 | 437.5 | 20 | <0.69 | 1:0.0457 |
| | >20000 | 30 | 218.75 | 10 | <0.34 | 1:0.0457 |
| | >20000 | 30 | 218.75 | 20 | <0.68 | 1:0.0914 |

A: Surf. E
B: BIOBAN P-1487
Media: 1/10TSB
Inoculum size: 5.727E+07CFU/ml

| | PPM AI MIC Values (24 hrs) | | | | | |
|---|---|---|---|---|---|---|
| Test | Alone | | Combination | | | |
| Organism | CA | CB | Ca | Cb | S.I. | Ratio (Ca:Cb) |
| Ps. aeruginosa | >20000 | 60 | 20000 | 50 | <1.83 | 1:0.0025 |
| ATCC# 15442 | >20000 | 60 | 10000 | 50 | <1.33 | 1:0.0050 |
| | >20000 | 60 | 5000 | 50 | <1.08 | 1:0.0100 |
| | >20000 | 60 | 2500 | 50 | <0.96 | 1:0.0200 |
| | >20000 | 60 | 1750 | 50 | <0.92 | 1:0.0286 |
| | >20000 | 60 | 875 | 50 | <0.88 | 1:0.0571 |
| | >20000 | 60 | 437.5 | 50 | <0.86 | 1:0.1143 |
| | >20000 | 60 | 218.75 | 50 | <0.84 | 1:0.2286 |

A: Surf. E
B: BIOBAN P-1487
Media: 1/10TSB
Inoculum size: 1.818E+06CFU/ml

| | PPM AI MIC Values (24 hrs) | | | | | |
|---|---|---|---|---|---|---|
| Test | Alone | | Combination | | | |
| Organism | CA | CB | Ca | Cb | S.I. | Ratio (Ca:Cb) |
| S. aureus | >20000 | 30 | 2500 | 20 | <0.79 | 1:0.0080 |
| ATCC# 6538 | >20000 | 30 | 437.5 | 20 | <0.69 | 1:0.0457 |

A: Surf. D
B: BIOBAN P-1487
Media: PDB
Inoculum size: 1.156E+06

| | PPM AI MIC Values (3rd day) | | | | | |
|---|---|---|---|---|---|---|
| Test | Alone | | Combination | | | |
| Organism | CA | CB | Ca | Cb | S.I. | Ratio (Ca:Cb) |
| A. niger | >20000 | 6 | 20000 | 0.6 | <1.10 | 1:0.0000 |
| ATCC# 16404 | >20000 | 6 | 10000 | 3 | <1.00 | 1:0.0003 |
| | >20000 | 6 | 5000 | 5 | <1.08 | 1:0.0010 |
| | >20000 | 6 | 2500 | 3 | <0.63 | 1:0.0012 |
| | >20000 | 6 | 1750 | 2 | <0.42 | 1:0.0011 |
| | >20000 | 6 | 875 | 5 | <0.88 | 1:0.0057 |
| | >20000 | 6 | 437.5 | 3 | <0.52 | 1:0.0069 |
| | >20000 | 6 | 218.75 | 4 | <0.68 | 1:0.0183 |

A: Surf. d
B: BIOBAN P-1487
Media: PDB
Inoculum size: 5.726E+05CFU/ml

| | PPM AI MIC Values (48 hrs) | | | | | |
|---|---|---|---|---|---|---|
| Test | Alone | | Combination | | | |
| Organism | CA | CB | Ca | Cb | S.I. | Ratio (Ca:Cb) |
| C. albicans | >20000 | 30 | 20000 | 3 | <1.10 | 1:0.0002 |
| ATCC# 10231 | >20000 | 30 | 10000 | 2 | <0.57 | 1:0.0002 |
| | >20000 | 30 | 10000 | 3 | <0.60 | 1:0.0003 |
| | >20000 | 30 | 10000 | 10 | <0.83 | 1:0.0010 |
| | >20000 | 30 | 10000 | 20 | <1.17 | 1:0.0020 |
| | >20000 | 30 | 5000 | 5 | <0.42 | 1:0.0010 |
| | >20000 | 30 | 5000 | 10 | <0.58 | 1:0.0020 |
| | >20000 | 30 | 5000 | 20 | <0.92 | 1:0.0040 |
| | >20000 | 30 | 2500 | 0.5 | <0.14 | 1:0.0002 |
| | >20000 | 30 | 2500 | 10 | <0.46 | 1:0.0040 |
| | >20000 | 30 | 2500 | 20 | <0.79 | 1:0.0080 |
| | >20000 | 30 | 1750 | 4 | <0.22 | 1:0.0023 |
| | >20000 | 30 | 1750 | 10 | <0.42 | 1:0.0057 |
| | >20000 | 30 | 1750 | 20 | <0.75 | 1:0.0114 |
| | >20000 | 30 | 875 | 20 | <0.71 | 1:0.0229 |
| | >20000 | 30 | 437.5 | 5 | <0.19 | 1:0.0114 |
| | >20000 | 30 | 437.5 | 10 | <0.36 | 1:0.0229 |
| | >20000 | 30 | 437.5 | 20 | <0.69 | 1:0.0457 |
| | >20000 | 30 | 218.75 | 8 | <0.28 | 1:0.0366 |
| | >20000 | 30 | 218.75 | 10 | <0.34 | 1:0.0457 |
| | >20000 | 30 | 218.75 | 20 | <0.68 | 1:0.0914 |

A: Surf. D
B: BIOBAN P-1487
Media: 1/10TSB
Inoculum size: 1.818E+05

| | PPM AI MIC Values (24 hrs) | | | | | |
|---|---|---|---|---|---|---|
| Test | Alone | | Combination | | | |
| Organism | CA | CB | Ca | Cb | S.I. | Ratio (Ca:Cb) |
| S. aureus | >20000 | 30 | 20000 | 20 | <1.67 | 1:0.0010 |
| ATCC# 6538 | >20000 | 30 | 10000 | 20 | <1.17 | 1:0.0020 |
| | >20000 | 30 | 5000 | 20 | <0.92 | 1:0.0040 |
| | >20000 | 30 | 2500 | 20 | <0.79 | 1:0.0080 |
| | >20000 | 30 | 1750 | 20 | <0.75 | 1:0.0114 |
| | >20000 | 30 | 218.75 | 20 | <0.68 | 1:0.0914 |

No synergy: *P. aeruginosa*

The following biocides had no synergy against any organism tested when paired with the following surfactants:
Surf. A
Sodium Benzoate, TRIS NITRO
Surf. E
DMDMH
Surf. D
CS-1246, OPP, DMDMH In the following combinations, the ratio of surfactant to biocide where synergy was observed were not commercially relevant, i.e., a ratio of 1:0.2 or greater (less biocide relative to surfactant). At these ratios, the biocide levels in a formulated product would be too low to be practical:
Surf. A
DIDAC, IPBC
Surf. E
CMIT/MIT, IPBC, OIT, TTPC, WSCP
Surf. D
CMIT/MIT, OIT, DIDAC (MBIT, IPBC, WSCP were synergistic only at 1:0.05 or worse except for one data point)

The invention claimed is:

1. A synergistic microbicidal composition comprising: (a) a nonionic surfactant with structure:

$$R^2O(CH_2CH(CH_3)O)_3(CH_2CH_2O)_5H$$

where $R^2$ is a mixture of $C_8$-$C_{14}$ linear alkyl groups; and (b) tetrahydro-3,5-dimethyl-2H-1,3,5-thiadiazine-2-thione; wherein a weight ratio of said nonionic surfactant to tetrahydro-3,5-dimethyl-2H-1,3,5-thiadiazine-2-thione is from 1:0.0024 to 1:0.4571.

2. The synergistic microbicidal composition of claim 1 in which said mixture of $C_8$-$C_{14}$ linear alkyl groups comprises from 60 to 75 wt % $C_8$-$C_{10}$ linear alkyl groups and 25 to 40 wt % $C_{12}$-$C_{14}$ linear alkyl groups.

* * * * *